United States Patent [19]

Lappe et al.

[11] Patent Number: 5,264,600

[45] Date of Patent: * Nov. 23, 1993

[54] PROCESS FOR THE RECOVERY OF RHODIUM FROM RESIDUES OF THE DISTILLATION OF PRODUCTS OF THE OXO SYNTHESIS

[75] Inventors: Peter Lappe, Dinslaken; Helmut Springer, Oberhausen, both of Fed. Rep. of Germany

[73] Assignee: Hoechst Aktiengesellschaft, Fed. Rep. of Germany

[*] Notice: The portion of the term of this patent subsequent to Feb. 25, 2009 has been disclaimed.

[21] Appl. No.: 855,731

[22] Filed: Mar. 20, 1992

[30] Foreign Application Priority Data

Mar. 28, 1991 [DE] Fed. Rep. of Germany ....... 4110212

[51] Int. Cl.$^5$ .............................................. C07F 15/00
[52] U.S. Cl. ....................................... 556/20; 556/22; 556/23; 556/136; 423/22
[58] Field of Search .................... 556/22, 136, 20, 23; 423/22

[56] References Cited

U.S. PATENT DOCUMENTS

| 4,196,096 | 4/1980 | Dawes et al. | 252/414 |
| 4,578,368 | 3/1986 | Zoeller | 502/28 |
| 5,091,546 | 2/1992 | Lappe et al. | 556/23 |

FOREIGN PATENT DOCUMENTS

| 255673 | 2/1988 | European Pat. Off. |
| 424736 | 5/1991 | European Pat. Off. |

*Primary Examiner*—Jose' G. Dees
*Assistant Examiner*—Porfirio Nazario-Gonzalez
*Attorney, Agent, or Firm*—Jordan B. Bierman

[57] ABSTRACT

Recovery of rhodium from the distillation residues from the crude products of oxo synthesis, the residue or the starting material containing the residue is treated with oxygen or an oxygen-containing gas in the presence of a monocarboxylic acid with 2 to 5 carbon atoms and of an alkali metal salt of a monocarboxylic acid with 2 to 5 carbon atoms. The rhodium is subsequently extracted with water as a water-soluble compound.

17 Claims, No Drawings

PROCESS FOR THE RECOVERY OF RHODIUM FROM RESIDUES OF THE DISTILLATION OF PRODUCTS OF THE OXO SYNTHESIS

This Application claims the priority of German 41 10 212.6, filed Mar. 28, 1991.

The present invention relates to an improved process for the recovery of rhodium from the residues obtained in the distillation of products of the oxo synthesis.

BACKGROUND OF THE INVENTION

The preparation of aldehydes and alcohols by the addition of carbon monoxide and hydrogen across olefinic double bonds (hydroformylation) is known. The reaction is catalyzed by metals of Group VIII of the Periodic Table (IUPAC version) or compounds thereof which, under the reaction conditions, form carbonyls or hydridocarbonyls. Whereas cobalt and cobalt compounds were formerly used almost exclusively as catalysts, at present, the use of rhodium, even though it costs much more than cobalt, has increased. For this purpose, rhodium is used alone or in combination with complexing agents, for example organic phosphines. Whereas the reaction pressures required for the oxo synthesis with rhodium as the catalyst are from 25 to 30 MPa, pressures of from 1 to 5 Mpa suffice when rhodium complex compounds are used.

Rhodium catalysts have distinct advantages. They have higher activity and selectivity and, moreover, make it possible to operate the plant without problems in many respects, especially as to the carrying out of the synthesis and the removal of the products from the reactor. Finally, the classical oxo process based on cobalt catalysts can, in many cases, be converted to rhodium catalysts using the same apparatus, thereby minimizing capital costs.

However, there are considerable difficulties in the loss-free—or at least substantially loss-free—removal and recovery of the rhodium, whether it is employed as catalyst with or without an additional complexing agent. After completion of the reaction, the rhodium is present in the hydroformylation product in the form of a solution of its carbonyl compound which may contain other ligands.

For workup, the pressure of the crude oxo product is normally reduced in several stages by initially reducing the synthesis pressure, which is about 1 to 30 MPa depending on the nature of the rhodium catalyst employed, to about 0.5 to 2.5 MPa. This releases the dissolved synthesis gas. Thereafter, it is possible to reduce the pressure to atmospheric. The rhodium is removed either immediately from the crude product or from the residue from the distillation of the crude product. The first route is followed when rhodium has been employed as the catalyst without additional complexing agent in the preceding hydroformylation stage; the second variant is applied when the rhodium catalyst contains other ligands in addition to carbon monoxide, for example phosphines or phosphites in complex linkages. It can also be used when, although the hydroformylation has been carried out with rhodium alone, a complexing agent has been added to the crude product after reducing the pressure to stabilize the rhodium. It is always necessary to take into account the fact that the noble metal is present in the crude product in a concentration of only a few ppm, and thus removal thereof must be carried out very carefully. Additional difficulties may arise due to the fact that, during the reduction in pressure, the rhodium, especially when it has been employed without a ligand, undergoes partial conversion into metallic form or forms polynuclear carbonyls. The result is the formation of a heterogeneous system which is composed of a liquid organic phase and a solid phase containing rhodium or rhodium compounds.

The recovery of rhodium from the products of the oxo synthesis including the residues of crude oxo products has been investigated many times. Such studies have led to the development of numerous processes, of which a few have also been used on an industrial scale.

U.S. Pat. No. 4,400,547 relates to the hydroformylation of olefins with 2 to 20 carbon atoms in the presence of unmodified rhodium as the catalyst. After completion of the reaction, a complex-forming compound such as triphenylphosphine is added to the crude oxo product, and the aldehyde is removed by distillation. The distillation residue is subsequently treated with oxygen in order to eliminate the ligand from the complex compound again and to recover the rhodium in active form. Separation of the rhodium from the distillation residue is not possible in this procedure.

The removal of noble metals such as rhodium from high-boiling hydroformylation residues is also described in U.S. Pat. No. 3,547,964. To do this, the residues are treated with hydrogen peroxide in the presence of acids such as formic acid, nitric acid, or sulfuric acid. However, there are limits to the industrial application of the process because of the high cost of hydrogen peroxide and the difficulties of handling it.

According to DE 24 48 005 C2, a rhodium-containing distillation residue is initially treated with acids and peroxides. Excess peroxides are subsequently decomposed by heating, and the aqueous solution containing the catalyst metal is reacted with hydrohalic acid or alkali metal halides and with tertiary phosphines and carbon monoxide, or compounds releasing carbon monoxide, in the presence of a water-soluble organic solvent. This procedure also requires the use of peroxides with the disadvantages described above, as well as the use of halogen-resistant materials.

Finally, U.S. Pat. No. 4,390,473 describes a process for the recovery of rhodium and cobalt from a solution which has been employed as catalyst in a low-pressure oxo process. To remove the complex-bound metals, aqueous formic acid is added to the solution, and an oxygen-containing gas is passed through. This results in two phases, an organic phase, and an aqueous phase which contains the metals dissolved as formates. After the phases have been separated, it is possible to obtain cobalt and rhodium from the aqueous solution. In practice, however, the reducing action of formic acid has proven very bothersome. This property resulted in the rhodium being partially deposited in metallic form, and no longer amenable to recovery.

BRIEF DESCRIPTION OF THE INVENTION

The object therefore was to develop a process which avoids the described disadvantages and ensures the maximum recovery of the noble metal in a really straightforward manner.

This object is achieved according to the invention by a process for the recovery of rhodium, which is contained in complex linkage with an organic phosphorus (III) compound in the residues of oxo synthesis distillation products, by treatment of the residue with oxygen or an oxygen-containing gas. The starting material containing the residue contains 10 to 1200 mol of aldehyde per g atom of rhodium, and is treated with oxygen or an oxygen-containing gas at 60° C. to 120° C. under atmospheric pressure or under elevated pressure. Also present are 1.0 to 15 mols of a 2 to 5 carbon monocarboxylic acid per g atom of rhodium and an alkali metal salt of a monocarboxylic acid with 2 to 5 carbon atoms. The reaction products are subsequently extracted with water to remove the rhodium as a water-soluble compound, and then the aqueous phase is separated from the organic phase.

The procedure according to the invention requires neither very expensive apparatus nor the use of costly chemicals. Despite comparatively little use of auxiliaries, it results surprisingly in the recovery of far more than 90% of the rhodium employed. The recovered rhodium can be used directly as catalyst or catalyst component in a hydroformylation reaction, without particular additional measures and, at the same time, it is ensured that formation of unwanted byproducts during the hydroformylation is substantially avoided.

The novel process starts from residues of the hydroformylation of olefinically unsaturated compounds such as those produced after removal of the hydroformylation products by distillation. They contain, besides varying amounts of aldehydes, essentially high molecular weight compounds which have been produced, inter alia, from aldehydes by aldol reaction and may, in a subsequent reaction, either form unsaturated compounds by elimination of water or result in the formation of aldehydes in a reverse aldol reaction.

It is important for the success of the process according to the invention that the aldehyde content in the residue, or in the starting material containing the residue, is limited. This is normally achieved by additional removal by distillation of aldehydic compounds. The residue treated in this way can be employed directly in the process according to the invention, provided that it is suitable for this purpose on the basis of its composition, in particular on the basis of its rhodium content. In most cases, the residue should be diluted by adding a solvent. The solution produced thereby is used as the starting material containing the residue.

DETAILED DESCRIPTION OF THE INVENTION

The residue or starting material containing the residue should contain not more than 1200, in particular 10 to 1200, preferably 30 to 1100, mols of aldehyde per g atom of rhodium. The limitation on the aldehyde content also depends, to a large extent, on the nature of the aldehyde contained in the residue o starting material. Relatively substantial removal of short-chain aldehydes with 3 to 5 carbon atoms is necessary, while long-chain aldehydes can be present in a larger amount. If the residue or the starting material containing it contains propionaldehyde, a ratio of from 10 to 500, in particular 20 to 400, preferably 30 to 300, mol of propionaldehyde per g atom of rhodium should be employed. If the residue or starting material containing the residue has methyl α-formylpropionate as the aldehyde, a ratio of from 100 to 800, in particular 200 to 700, preferably 300 to 600, mols of aldehyde per g atom of rhodium is permissible. In the case of an aldehyde with 9 carbon atoms (prepared by hydroformylation of diisobutylene), the ratio can be 600 to 1200, in particular 700 to 1150, preferably 800 to 1100, mols of aldehyde per g atom of rhodium.

Higher aldehyde contents generally result in a distinct deterioration in the recovery of rhodium and, moreover, require large increases in the amounts to be added of both the carboxylic acid and of the carboxylic acid salt. This has an unfavorable effect, however, on the reusability of the recovered rhodium as a hydroformylation catalyst or component thereof.

The nature of the compounds which have been hydroformylated is irrelevant to the claimed procedure. Accordingly, it is possible to employ residues resulting from the reaction of olefins with carbon monoxide and hydrogen, as well as high molecular weight products which are produced from the reaction of olefinically unsaturated compounds which, besides the double bond, also contain functional groups in the molecule. However, the novel process is principally aimed at the recovery of rhodium from the residues of the hydroformylation of olefins with 2 to 12 carbon atoms, in accordance with the economic importance of the aldehydes prepared from them.

Besides saturated and unsaturated condensation products, the residues may also contain compounds which react with the rhodium ions to form complexes, and are usually in excess compared to the rhodium. These compounds include organic phosphorus (III) compounds, especially phosphines and phosphites, preferably the aryl compounds such as triphenylphosphine and triphenyl phosphite. Their purpose is to improve the selectivity of the reaction by forming stable complex compounds during the reaction, and to prevent the deposition of metallic rhodium after the reaction. The ratio of ligand to rhodium in the reaction mixture is 2 to 150, in particular 5 to 50, mols per g atom. Because of their low volatility, both components are also present in the distillation residue in approximately the same ratio, the rhodium concentration being between 30 and 1000 ppm by weight, in particular 100 to 500 ppm by weight.

According to the invention, the distillation residue, or starting material containing it, is treated with oxygen. The oxidizing agent is employed in pure form or as oxygen-containing gas mixture, in particular air. The amount of oxygen can vary within wide limits. It is preferably governed by the amount of starting material. It is advisable to use 1 to 10, in particular 2 to 6, mols of oxygen per kg of starting material.

In accordance with the invention, the treatment of the distillation residue or the starting material containing it with oxygen takes place in the presence of a saturated, straight or branched chain monocarboxylic acid with 2 to 5 carbon atoms. Examples of suitable acids are acetic, propionic, n-butyric, i-butyric, and n-valeric. Acetic acid and propionic acid have proven particularly suitable. They are employed in their commercially available forms and in an amount such that about 1.0 to 15, in particular 1.2 to 10, preferably 1.5 to 6, mols are present per g atom of rhodium. The acid is added to the residue or starting material containing it before the reaction with oxygen, regardless of whether it is possible for acid to be formed during the reaction from the residue itself, because of the limited amount of aldehyde still present in the residue. The exact mechanism of the acid reaction is unknown. Various observations suggest that it carries out an initiator function, i.e. has a crucial effect on the initiation of the reaction.

Another feature of the process according to the invention, which is likewise very important, is the presence of an alkali metal carboxylate in the residue or starting material while oxygen is passed into the mixture of the high-boiling compounds. As in the case of the monocarboxylic acid, the nature of the intervention of the salt in the progress of the reaction is not clear. However, the addition of carboxylate results in a distinct increase in the recovered amount of the rhodium, i.e. a further reduction in the rhodium remaining dissolved in the organic phase.

Employed as alkali metal carboxylates within the scope of the novel process are salts of saturated, straight or branched chain monocarboxylic acids with 2 to 5 carbon atoms. The sodium and potassium salts of acetic acid, propionic acid, n- and iso-butyric acid, and n-valeric acid have proven particularly suitable. They are used in an amount of from 10 to 100, in particular 12 to 50, preferably 12 to 30, mol per g atom of rhodium. The commercially available salts are suitable, but they only gradually dissolve during the course of the oxidation. It is therefore more advantageous to add the residual free acid and the equivalent amount of alkali metal hydroxide to the residue or starting material; they immediately form a homogeneous solution and thus are fully active.

The reaction of the residue with oxygen is carried out at 60° C. to 120° C., in particular 70° C. to 105° C., preferably 80° C. to 100° C. It can be carried out under atmospheric pressure or under elevated pressure; pressures between 0.2 and 1.0 MPa have proven particularly suitable.

In a preferred embodiment of the novel process, the starting material to be treated with oxygen contains rhodium in a concentration of about 200 or less, in particular 20 to 200, preferably 30 to 150, ppm by weight. It has been found that the amounts of rhodium remaining in the residues, after they have been treated according to the invention, are particularly low when the rhodium concentration in the original solution (starting material) is within the foregoing ranges. It is, therefore, advisable for residues in which the rhodium concentration is more than about 300 ppm by weight to be diluted appropriately and to use these solutions as the starting material. Particularly suitable diluents are higher boiling aliphatic or aromatic hydrocarbons, for example toluene and xylene, hydrocarbon mixtures, or distillation residues from which the rhodium catalyst has been removed.

The reaction time depends on the concentration of rhodium and of ligand in the distillation residue. It is also determined by the amount of oxygen employed and by the reaction temperature and pressure. High concentrations of dissolved substances require longer treatment times than low concentrations. The reaction time is reduced by a large oxygen supply, elevated pressure, and vigorous mixing of the residue with oxygen. Temperatures in the lower and upper region of the claimed range are somewhat less effective than in the middle of the temperature range.

The reaction of the distillation residue can be carried out continuously or batchwise in conventional apparatus. The oxygen or the oxygen-containing gas is passed through distributor devices into the reactor, and uniform mixing of liquid and gaseous phase is assisted, where appropriate, by stirring.

After conclusion of the treatment with oxygen, the organic phase is extracted with water. The procedure is carried out at room temperature or elevated temperature, for example 50° C. to 90° C., in one or, more expediently, in several stages. The amount of water employed depends on the partition equilibrium of the substance to be extracted between the organic and aqueous phase and on the required rhodium concentration in the aqueous phase. The aqueous solution of the rhodium compound can also be used repeatedly for the extraction by recycling, thereby to achieve an enrichment of the metal in the solution. The aqueous solution can be used directly for catalyst preparation without additional purification steps.

The following examples illustrate the invention without restricting it to these embodiments.

The starting materials (residues) are characterized by their essential distinctive numbers in the following table.

TABLE

| | Residues from propionaldehyde synthesis | | | | | | comparison | | | | MAFP* comparison | | i-C9-aldeh.** comparison | | |
|---|---|---|---|---|---|---|---|---|---|---|---|---|---|---|---|
| | A | B | C | D | E | F | G | H | I | J | K | L | M | N | O |
| Rh content (ppm by wt.) | 516 | 504 | 992 | 374 | 537 | 338 | 110 | 155 | 177 | 209 | 430 | 334 | 251 | 191 | 154 |
| P(III) content (mmol/kg) | 64 | 85 | 75 | 51 | 61 | 46 | 17 | 22 | 28 | 24 | 13 | 10 | 61 | 48 | 33 |
| P total (mmol/kg) | 97 | 91 | 131 | 70 | 92 | 48 | 18 | 29 | 33 | 28 | 33 | 24 | 65 | 51 | 37 |
| Neutralizion No. (mg KOH/g) | 18 | 19 | 17 | 14 | 19 | 15 | — | 9 | 10 | 10 | 66 | 46 | 10 | 10 | 8 |
| Water (%) | 0.21 | 0.18 | 0.26 | 0.17 | 0.17 | 0.14 | 0.09 | 0.10 | 0.10 | 0.10 | 0.04 | 0.08 | 0.27 | 0.19 | 0.16 |
| Aldehydic components (mmol/kg) | 871 | 1022 | 457 | 1063 | 846 | 1160 | 2137 | 3008 | 2566 | 2669 | 2155 | 5510 | 2391 | 3501 | 4182 |
| Aldehyde:Rh ratio (mol/g atom) | 174 | 209 | 47 | 292 | 162 | 353 | 1999 | 1997 | 1492 | 1314 | 516 | 1697 | 980 | 1886 | 2792 |

*Residue from the synthesis of methyl α-formylpropionate (hydroformylation of methyl acrylate)
**Residue from the synthesis of i-nonyl aldehyde (hydroformylation of dissobutylene)

Residues A to J originate from the preparation of propionaldehyde, residues K to M originate from the preparation of methyl α-formylpropionate (MAFP), and residues M to O originate from the preparation of i-nonyl aldehyde. By starting material is meant the mixture of the distillation residue and solvent employed in each case.

EXAMPLE 1

Residue from propionaldehyde synthesis

| Starting materials: | |
| --- | --- |
| Distillation residue A: | 81.4 g (= 42 mg Rh) |
| Xylene: | 518.6 g |
| NaOH (30% strength solution): | 1.36 g (10.2 mmol) |
| Propionic acid (99.5% pure): | 0.86 g (11.6 mmol) |
| Ratio Rh (g atom) carboxylic acid (mol)/carboxylic acid salt (mol): | 1:3:25 |

The above-mentioned starting materials are placed in a 1 liter glass autoclave provided with a heating jacket and heated with stirring to 95° C. over the course of 15 minutes. Subsequently 50 liters of air per hour are passed in through an immersed tube under a pressure of 0.35 MPa for a period of 6 hours (corresponding to 4.0 mols of $O_2$/kg of starting material). The reaction takes place at a constant internal pressure of 0.35 MPa and a constant temperature of 100° C. The off-gas is removed through a needle valve in the lid of the autoclave and passed into a flask fitted with condenser.

After conclusion of the reaction, the contents of the autoclave are cooled to 80° C. over the course of about 15 minutes, and the supply of air is stopped. The pressure is reduced, 600 g of water are added to the reaction mixture, and the mixture is stirred at 70° C. to 80° C. for a further 15 minutes and removed from the autoclave. The aqueous phase is separated from the organic phase and the organic phase is extracted once more with 600 g of water.

The organic phase contains 0.72 mg of Rh, i.e. 1.7% by weight of the rhodium originally employed.

EXAMPLE 2

Residue from propionaldehyde synthesis

| Starting materials: | |
| --- | --- |
| Distillation residue B: | 83.3 g (= 42 mg Rh) |
| Xylene: | 516.7 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 but with 40 liters of air per hours (corresponding to 3.2 mols of $O_2$/kg of starting material).

The organic phase contains 1.32 mg of Rh, i.e. 3.1% by weight of the rhodium originally employed.

EXAMPLE 3

Residue from propionaldehyde synthesis

| Starting materials: | |
| --- | --- |
| Distillation residue C: | 42.3 g (= 42 mg Rh) |
| Xylene: | 557.7 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 but with 38 liters of air per hours (corresponding to 3.0 mols of $O_2$/kg of starting material).

The organic phase contains 0.28 mg of Rh, i.e. 0.7% by weight of the rhodium originally employed.

EXAMPLE 4

Residue from propionaldehyde synthesis

| Starting materials: | |
| --- | --- |
| Distillation residue D: | 112.3 g (= 42 mg Rh) |
| Xylene: | 487.7 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 but with 45 liters of air per hours (corresponding to 3.6 mols of $O_2$/kg of starting material).

The organic phase contains 0.89 mg of Rh, i.e. 2.1% by weight of the rhodium originally employed.

EXAMPLE 5

Residue from propionaldehyde synthesis

| Starting materials: | |
| --- | --- |
| Distillation residue E: | 78.2 g (= 42 mg Rh) |
| Xylene: | 521.8 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 but with 30 liters of air per hour (corresponding to 2.4 mols of $O_2$/kg of starting material).

The organic phase contains 0.26 m of Rh, i.e. 0.6% by weight of the rhodium originally employed.

EXAMPLE 6

Residue from propionaldehyde synthesis

| Starting materials: | |
| --- | --- |
| Distillation residue E: | 156.4 g (= 84 mg Rh) |
| Xylene: | 443.6 g |
| NaOH (30% strength solution): | 2.72 g (20.4 mmol) |
| Propionic acid (99.5% pure): | 1.72 g (23.2 mmol) |
| Ratio Rh (g atom)/carboxylic acid (mol)/carboxylic acid salt (mol): | 1:3:25 |

The procedure is as described in Example 1.

The organic phase contains 2.09 mg of Rh, i.e. 2.5% by weight of the rhodium originally employed.

EXAMPLE 7

Residue from propionaldehyde synthesis

| Starting materials: | |
| --- | --- |
| Distillation residue E: | 234.6 g (= 126 mg Rh) |
| Xylene: | 365.4 g |
| NaOH (30% strength solution): | 4.08 g (30.6 mmol) |
| Propionic acid (99.5% pure): | 2.58 g (34.7 mmol) |
| Ratio Rh (g atom)/carboxylic acid (mol)/carboxylic acid salt (mol): | 1:3:25 |

The procedure is as described in Example 1.

The organic phase contains 4/34 mg of Rh, i.e. 3.4% by weight of the rhodium originally employed.

EXAMPLE 8

Residue from propionaldehyde synthesis

| Starting materials: | |
|---|---|
| Distillation residue F: | 124.3 g (= 42 mg Rh) |
| Toluene: | 475.7 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1, but at 95° C.

The organic phase contains 1.29 mg of Rh, i.e. 3.1% by weight of the rhodium originally employed.

EXAMPLE 9

Residue from propionaldehyde synthesis

| Starting materials: | |
|---|---|
| Distillation residue G: | 381.8 g (= 42 mg Rh) |
| Xylene: | 218.2 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1.

The organic phase still contains 4.49 mg of Rh, i.e. 10.7% by weight of the rhodium originally employed. The aldehyde (mol):Rh (g atom) ratio is 1999 (cf. Table).

EXAMPLE 10 (COMPARATIVE)

Residue from propionaldehyde synthesis

| Starting materials: | |
|---|---|
| Distillation residue H: | 271 g (= 42 mg Rh) |
| Xylene: | 329 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1.

The organic phase still contains 2.94 mg of Rh, i.e. 7.0% by weight of the rhodium originally employed. The aldehyde:Rh ratio is 1997 (cf. Table).

EXAMPLE 11 (COMPARATIVE)

Residue from propionaldehyde synthesis

| Starting materials: | |
|---|---|
| Distillation residue I: | 237.3 g (= 42 mg Rh) |
| Toluene: | 362.7 g |
| NaOH (30% strength solution): | 8.16 g (61.2 mmol) |
| Propionic acid (99.5% pure): | 5.14 g (69.2 mmol) |
| Ratio Rh (g atom)/carboxylic acid (mol)/carboxylic acid salt (mol): | 1:20:150 |

The procedure is as described in Example 1 but with 45 liters of air per hours (corresponding to 3.6 mols of $O_2$/kg of starting material).

The organic phase still contains 3.97 mg of Rh, i.e. 9.5% by weight of the rhodium originally employed. The aldehyde (mol):Rh (g atom) ratio is 1492 (cf. Table).

EXAMPLE 12 (COMPARATIVE)

Residue from propionaldehyde synthesis

| Starting materials: | |
|---|---|
| Distillation residue J: | 201 g (= 42 mg Rh) |
| Toluene: | 399 g |
| NaOH (30% strength solution): | 8.16 g (61.2 mmol) |
| Propionic acid (99.5% pure): | 5.14 g (69.1 mmol) |
| Ratio Rh (g atom)/carboxylic acid (mol)/carboxylic acid salt (mol): | 1:20:150 |

The procedure is as described in Example 1 but with 40 liters of air per hours (corresponding to 3.2 mols of $O_2$/kg of starting material).

The organic phase still contains 2.89 mg of Rh, i.e. 6.9% by weight of the rhodium originally employed. The aldehyde (mol):Rh (g atom) ratio is 1314 (cf. Table).

EXAMPLE 13

Residue from methyl α-formylpropionate synthesis

| Starting materials: | |
|---|---|
| Distillation residue K: | 97.7 g (= 42 mg Rh) |
| Xylene: | 502.3 g |
| NaOH (30% strength solution): | 12.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 bu at 80° C. and with 40 liters of air per hour (corresponding to 3.2 mols of $O_2$/kg of starting material).

The organic phase contains 1.39 mg of Rh, i.e. 3.3% by weight of the rhodium originally employed.

EXAMPLE 14

Residue from methyl α-formylpropionate synthesis

| Starting materials: | |
|---|---|
| Distillation residue K: | 97.7 g (= 42 mg Rh) |
| Xylene: | 502.3 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 but a 95° C. and with 40 liters of air per hour (corresponding to 3.2 mols of $O_2$/kg of starting material).

The organic phase still contains 0.31 mg of Rh, i.e. 0.7% by weight of the rhodium originally employed.

EXAMPLE 15 (COMPARATIVE)

Residue from methyl α-formylpropionate synthesis

| Starting materials: | |
|---|---|
| Distillation residue L: | 125.7 g (= 42 mg Rh) |
| Xylene: | 474.3 g |

-continued

Starting materials:

| | |
|---|---|
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:3:25 |

The procedure is as described in Example 1 but at 80° C. and with 40 liters of air per hour (corresponding to 3.2 mols of $O_2$/kg of starting material).

The organic phase still contains 3.79 mg of Rh, i.e. 9.0% by weight of the rhodium originally employed. The aldehyde (mol):Rh (g atom) ratio is 1697 (cf. Table).

EXAMPLE 16

Residue from i-nonyl aldehyde synthesis

Starting materials:

| | |
|---|---|
| Distillation residue M: | 159.1 g (= 40 mg Rh) |
| Toluene: | 440.9 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:4:26 |

The procedure is as described in Example 1 but a 90° C. and with 40 liters of air per hour (corresponding to 3.2 mols of $O_2$/kg of starting material).

The organic phase contains 1.26 mg of Rh, i.e. 3.2% by weight of the rhodium originally employed.

EXAMPLE 17

Residue from i-nonyl aldehyde synthesis

Starting materials:

| | |
|---|---|
| Distillation residue M: | 159.1 g (= 40 mg Rh) |
| Toluene: | 440.9 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:4:26 |

The procedure is as described in Example 1 but with 40 liters of air per hour (corresponding to 3.2 mols of $O_2$/kg of starting material).

The organic phase contains 0.8 mg of Rh, i.e. 2.0% by weight of the rhodium originally employed.

EXAMPLE 18

Residue from i-nonyl aldehyde synthesis

Starting materials:

| | |
|---|---|
| Distillation residue M: | 159.1 g (= 40 mg Rh) |
| Toluene: | 440.9 g |
| NaOH (30% strength solution): | 0.82 g (6.15 mmol) |
| Propionic acid (99.5% pure): | 0.52 g (7.0 mmol) |
| Ratio Rh (g atom)/carboxylic acid (mol)/carboxylic acid salt (mol): | 1:2:16 |

The procedure is as described in Example 1 but with 40 liters of air per hour (corresponding to 3.2 mols of $O_2$/kg of starting material).

The organic phase contains 1.39 mg of Rh, i.e. 3.5% by weight of the rhodium originally employed.

EXAMPLE 19

Residue from i-nonyl aldehyde synthesis

Starting materials:

| | |
|---|---|
| Distillation residue N: | 209.1 g (= 40 mg Rh) |
| Toluene: | 390.9 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:4:26 |

The procedure is as described in Example 1 but with 40 liters of air per hour (corresponding to 3.2 mols of $O_2$/kg of starting material).

The organic phase still contains 2.89 mg of Rh, i.e. 7.2% by weight of the rhodium originally employed. The aldehyde (mol):Rh (g atom) ratio is 1886 (cf. Table).

EXAMPLE 20 (COMPARATIVE)

Residue from i-nonyl aldehyde synthesis

Starting materials:

| | |
|---|---|
| Distillation residue N: | 259.1 g (= 40 mg Rh) |
| Toluene: | 340.9 g |
| NaOH (30% strength solution): | 1.36 g (10.2 mmol) |
| Propionic acid (99.5% pure): | 0.86 g (11.6 mmol) |
| Ratio Rh (g atom)/carboxylic acid (mol)/carboxylic acid salt (mol): | 1:4:26 |

The procedure is as described in Example 1 but with 40 liters of air per hour (corresponding to 3.2 mols of $O_2$/kg of starting material).

The organic phase still contains 5.23 mg of Rh, i.e. 13.1% by weight of the rhodium originally employed. The aldehyde (mol):R h (g atom) ratio is 2792 (cf. Table).

What we claim is:

1. A process for the recovery of rhodium, which is contained in complex linkage with an organic phosphorus (III) compound in residues of distillation of products of the oxo synthesis, comprising contacting a starting material containing said residues with oxygen or an oxygen-containing gas, wherein said starting material contains 10 to 1200 mol of aldehyde per g atom of rhodium, and treatment of said starting material with oxygen or an oxygen containing gas at 60° C. to 120° C. under at least atmospheric pressure in the presence of 1.0 to 15 mol of a 2 to 5 carbon monocarboxylic acid per g atom of rhodium and in the presence of an alkali metal salt of a monocarboxylic acid with 2 to 5 carbon atoms, followed by extraction with water to remove said rhodium as a water-soluble compound and form an aqueous phase and an organic phase, and thereafter separating said aqueous phase from said organic phase.

2. The process of claim 1 wherein said oxygen-containing ga is air.

3. The process of claim 1 wherein there are 1 to 10 mol of oxygen per kg of said starting material.

4. The process of claim 3 wherein there are 2 to 6 mols of oxygen per kilogram of said starting material.

5. The process of claim 1 which comprises adding to said starting material an acid selected from the group consisting of acetic, propionic, n-butyric, i-butyric, n-valeric, and sodium or potassium salts thereof.

6. The process of claim 1 wherein an acid amount of 1.2 to 10 mols of said monocarboxylic acid per g atom of rhodium are added to said starting material.

7. The process of claim 6 wherein said acid amount is 1.5 to 6 mols of said monocarboxylic acid per g atom of rhodium.

8. The process of claim 1 wherein there are 10 to 100 mols of said alkali metal salt per g atom of rhodium added to said starting material.

9. The process of claim 8 wherein there are 15 to 50 mols of said alkali metal salt per g atom of rhodium added to said starting material.

10. The process of claim 9 wherein there are 12 to 30 mols of said alkali metal salt per g atom of rhodium added to said starting material.

11. The process of claim 1 wherein said treatment is carried out at a treatment temperature of 70° C. to 105° C.

12. The process of claim 11 wherein said treatment temperature is 80° C. to 100° C.

13. The process of claim 1 wherein said pressure is from 0.2 to 1.0 MPa.

14. The process of claim 1 wherein said rhodium is present in said starting material in a concentration not exceeding about 300 ppm by weight.

15. The process of claim 14 wherein said concentration is 20 to 200 ppm by weight.

16. The process of claim 15 wherein said concentration is 30 to 150 ppm by weight.

17. The process of claim 5 wherein said acid is acetic or propionic.

* * * * *